United States Patent [19]

Dobler et al.

[11] Patent Number: 5,773,635
[45] Date of Patent: Jun. 30, 1998

[54] PREPARATION OF POLYENECARBONYL COMPOUNDS HAVING A HIGH CONTENT OF THE ALL-E ISOMER, AND OF THEIR ACETALS OR KETALS

[75] Inventors: Walter Dobler, Heidelberg; Wolfgang Krause, Brühl; Joachim Paust, Neuhofen; Otto Wörz, Friedelsheim; Udo Rheude, Otterstadt; Wolfram Burst, Mannheim; Günter Däuwel, Lustadt; Armin Bertram, Frankenthal; Bernhard Schulz, Schwetzingen; Günter Wegner; Peter Münster, both of Römerberg; Hansgeorg Ernst, Speyer; Arno Kochner, Waldsee; Heinz Etzrodt, Neustadt, all of Germany

[73] Assignee: BASF Aktiengesellschaft, Ludwigshafen, Germany

[21] Appl. No.: 498,840

[22] Filed: Jul. 6, 1995

[51] Int. Cl.$^6$ ..................................... C07C 51/16
[52] U.S. Cl. .................. 554/134; 554/132; 554/139; 568/309; 568/320; 568/338; 568/344; 549/357; 549/430; 423/405
[58] Field of Search ................... 554/127, 132, 554/139; 568/309, 320, 338, 344; 549/357, 430; 423/405

[56] References Cited

FOREIGN PATENT DOCUMENTS 1143657  9/1979  Canada .
92/00360  1/1992  WIPO .

OTHER PUBLICATIONS

Chemical Abstracts, 119: 23870, 1993, Compounds Attached.

Handbuch zur Anwendung der . . . 853–858.

Xenobiotica, 1979, vol. 9, No. 11, 649–657, J. U. Skaare and E. Solheim.

Ortho–Chinone, C. Grundmann, 3–6.

J. Org. Chem. 30 (1965) p. 2481.

Pure & Appl. Chem. vol. 63, No. 1, 45–58, 1991, Paust.

Houben–Weyl, Methoden Der Organischem, 1972, 127–129 and 142–144.

*Primary Examiner*—Gary Geist
*Assistant Examiner*—Deborah D. Carr
*Attorney, Agent, or Firm*—Keil & Weinkauf

[57] ABSTRACT

A process for preparing polyenecarbonyl compounds having a high all-E content and their acetals or ketals by aldol condensation or Horner-Emmons reaction comprises carrying out the reaction, for the purposes of the preferred formation of a double bond of E configuration and in order to maintain the E configuration of the double bonds in the stating compounds as completely as possible, in the presence of oxygen or an oxygen-inert gas mixture or nitric oxide or a nitric oxide-inert gas mixture and/or in the presence of specific stable radicals and/or in the presence of quinones or quinone derivatives.

12 Claims, No Drawings

PREPARATION OF POLYENECARBONYL COMPOUNDS HAVING A HIGH CONTENT OF THE ALL-E ISOMER, AND OF THEIR ACETALS OR KETALS

BACKGROUND OF THE INVENTION

1. Field of the Invention

The invention relates to an improved process for preparing poly-encarbonyl compounds having a high all-E content, and their acetals or ketals, in particular carotenoids, such as β-apo-8'-caro-tenic acid esters, citranaxanthin and neurosporaxanthin esters.

Polyenes are very generally understood as meaning unsaturated aliphatic hydrocarbons having three or more conjugated double bonds in the molecule, ie. compounds containing numerous alternating single and double bonds. Polyenecarbonyl compounds are defined as polyenes which have a carbonyl group conjugated to the polyene chain.

Many polyenes and polyenecarbonyl compounds have gained interest as biologically active medicinal compounds or as food colorants and feed additives.

2. Description of the Related Art

According to their importance, numerous methods for preparing polyenes and polyenecarbonyl compounds have been developed (for survey cf. O. Isler in Carotenoids, Birkhauser-Verlag, 1971).

Known methods for preparing polyenes are, for example, the Horner-Emmons reaction, ie. the coupling of aldehydes and ketones to appropriate phosphonic acid esters in the presence of bases (cf. Houben-Weyl, Methoden der Organischen Chemie [Methods of Organic Chemistry] 5/ld (1972) pages 127 to 129 or Pure & Appl. Chem. Vol. 63 (1991), No. 1, pages 45–48) and the aldol condensation, ie. the base-catalyzed coupling of ketones and/or aldehydes to CH-acidic compounds to give β-hydroxycarbonyl compounds and subsequent elimination of water with formation of a system of conjugated double bonds (cf. Houben-Weyl 5/ld (1972) pages 142–144 or J. Org. Chem. 30 (1965) page 2481). C-C couplings of this type with formation of a double bond can lead to double bonds of Z or E configuration. In the processes known until now, products were in general obtained which only consisted of all-E isomers to an unsatisfactory extent. As most of the desired natural polyenecarbonyl compounds have the all-E configuration, it is expedient to start from all-E polyene building blocks and to carry out the C-C coupling under reaction conditions which preferably lead to a double bond of E configuration, and to prevent isomerization of the polyene building blocks to Z isomers as completely as possible.

It was therefore the object of the invention to find reaction conditions under which the coupling of polyene building blocks to polyenecarbonyl compounds preferably proceeds with formation of a double bond of E configuration and with retention of the E configuration of the double bonds in the starting material.

SUMMARY OF THE INVENTION

It has now surprisingly been found that in said olefin coupling reactions a coupling in the E configuration with retention of the E configuration in the starting compounds is preferably obtained if the reaction is carried out in the presence of oxygen, nitric oxide, certain sizable radicals or radical scavengers and/or in the presence of certain quinones, quinone derivatives or coenzyme Q10 hydroxyquinone.

DESCRIPTION OF THE PREFERRED EMBODIMENTS

The present invention accordingly relates to a process for preparing polyenecarbonyl compounds having a high all-E content or their acetals or ketals by a Horner-Emmons reaction or an aldol condensation of a suitable carbonyl compound with a suitable dialkyl phosphonate or of a suitable CH-acidic compound, which comprises carrying out the reaction, for the purposes of the preferred formation of a double bond having E configuration and in order to maintain the E configuration of the double bonds in the starting compounds as completely as possible, in the presence of oxygen or an oxygen-inert gas mixture, or in the presence of nitric oxide or a nitric oxide-inert gas mixture and/or in the presence of a stable radical of the formula I

where $R^6$ and $R^7$ are a $C_1$- to $C_4$-alkyl group or else $R^6$ and $R^7$ are an ethylene group, propylene group, vinylene group or propenylene group, which can be substituted by alkyl, aryl, hydroxyl, alkoxy, silyloxy, oxo, amino, mercapto, alkylmercapto, cyano, carboxyl or aminocarbonyl (carbamoyl), heteroaryl or alkylcarbonyloxy groups;

and/or in the presence of a stable radical of the formula II

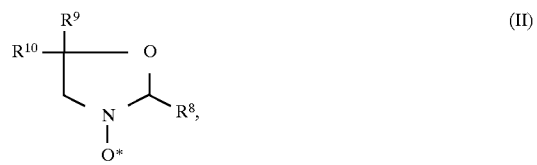

where $R^8$, $R^9$ and $R^{10}$ can have the meanings indicated above for $R^6$ and $R^7$;

and/or in the presence of the stable radical 2,2-diphenyl-1-pic-rylhydrazyl, or a hydrogen peroxide-urea adduct and/or in the presence of quinones, quinone derivatives or coenzyme Q10 hydroquinone, the oxygen, the nitric oxide, said stable radicals or the hydrogen peroxide-urea adduct, the quinones, quinone derivatives or coenzyme Q10 hydroquinone being used in amounts from 0.3 to 10 mol %, preferably 0.5–6 mol %, in particular 1.0 to 5 mol %, based on the carbonyl compound employed.

For example, polyenecarbonyl compounds of the formula III, their acetals or ketals can be prepared by the process according to the invention.

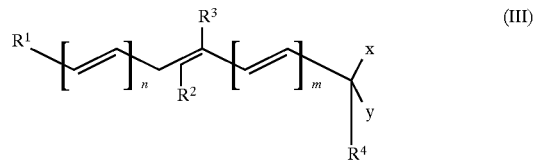

In this formula, $R^1$ to $R^4$ are hydrogen or organic radicals; n is an integer from 0 to 20, in particular 3–10; m is an integer from 0 to 20, in particular 0 to 10, m+n being at least 2; X and Y are a $C_1$- to $C_4$-alkoxy group, in particular a methoxy or ethoxy group, or else X and Y together are oxygen or a radical —O—CH$_2$—CH$_2$—O—, —O—CH$_2$—C(CH$_3$)$_2$—CH$_2$—O—, —O—CH=CH—O— or —O—CH$_2$—CH$_2$—CH$_2$—O— which may be substituted by one or more methyl groups. The hydrogen atoms in the brackets can be partly substituted by organic radicals, preferably alkyl groups, in particular a methyl group.

Suitable polyene building blocks are accordingly, for example, carbonyl compounds of the formula IV

(IV)

where $R^1$ and $R^2$ are hydrogen or organic radicals, n is an integer from 0 to 20, in particular 3 to 10, and the hydrogen atoms on the double bonds within the brackets can also be replaced by organic radicals.

The carbonyl compounds of the general formula IV used as starting compounds are generally known compounds. Suitable polyene building blocks are eg. compounds of the formula IV where $R^1$ and $R^2$ are hydrogen, alkyl, alkoxy, cycloalkyl, cycloalkenyl or phenyl groups, it being possible for the cycloalkyl, cycloalkenyl and phenyl groups to be additionally substituted, for example by alkyl, hydroxyl, oxo, amino, carboxyl, carbamoyl, alkylcarbonyloxy or cyano groups or alternatively by halogen.

$R^1$ is preferably the following cycloalkenyl groups

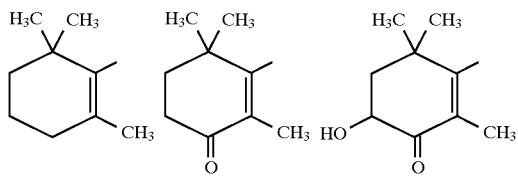

or else a formyl group while $R^2$ is preferably hydrogen or alkyl.

The number of double bonds in the compounds of the formula IV (termed n) is preferably from 2 to 15, in particular from 3 to 10. The double bonds within the brackets can in particular carry $C_1$- to $C_4$-alkyl groups, preferably methyl groups, as organic radicals. Suitable carbonyl compounds which may be mentioned are, for example: β-apo-12'-carotenal ($C_{25}$-aldehyde), β-apo-8'-carotenal ($C_{30}$-aldehyde), retinal ($C_{20}$-aldehyde), 2,7-dimethyl-2,4,6-octa-trienedial ($C_{10}$-dialdehyde), crocetindialdehyde ($C_{20}$-dialdehyde) and β-apo-4'-carotenal ($C_{35}$-aldehyde).

When using dialdehydes, compounds of the formula IX

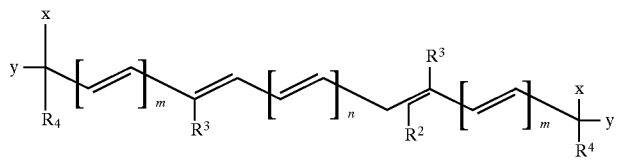

can also be formed by reaction with 2 mol of the compounds of the formula V.

To prepare polyenecarbonyl compounds of the formula III preferably having the all-E configuration, the compounds of the formula IV must also preferably have the all-E configuration.

The carbonyl compounds and their acetals or ketals of the formula V are also generally known compounds. Suitable compounds are especially those of the formula V

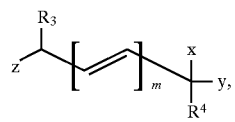
(V)

where $R^3$ and $R^4$ are organic radicals, m is an integer from 0 to 20, preferably 0 to 10, X and Y are a $C_1$–$C_4$-alkyl group, in particular a methyl group or ethyl group, or else X and Y together are oxygen or a radical —O—CH$_2$—CH$_2$—O—, —O—CH$_2$—C(CH$_3$)$_2$—CH$_2$—O—, —O—CH=CH—O— or —O—CH$_2$—CH$_2$—CH$_2$—O— which may be substituted by one or more methyl groups and Z is hydrogen or a dialkylphosphono group, in particular —PO(OCH$_3$)$_2$ or —PO(OC$_2$H$_5$)$_2$. The number of double bonds (termed m) can be 0 (as in acetone), but also up to 20, preferably from 0 to 10. $R^3$ is hydrogen, or an alkyl, alkoxy, cycloalkyl, cycloalkenyl or phenyl group which can also be substituted by other radicals, such as $C_1$–$C_4$-alkyl, hydroxyl, alkoxy, silyloxy, oxo, amino, cyano, carboxyl, carbamoyl or alkylcarbonyloxy groups.

$R^4$, and also $R^3$, is preferably hydrogen, $C_1$–to $C_4$-alkyl or $C_1$ to $C_4$-alkoxy groups.

When carrying out a Horner-Emmons reaction, polyene compounds of the formula III, however, can also be obtained by using polyene building blocks which in each case contain the reacting groups on the other building block, ie. compounds of the general formula IV where, instead of the group

a group

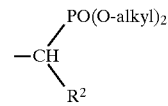

is contained, are reacted with compounds of the formula V where, instead of the group

the group

is contained.

Carbonyl compounds of the general formula V which may be mentioned are, for example:

acetone, ethyl 4-dimethylphosphono-2-methyl-2-butenoate, ethyl 4-diethylphosphono-2-methylbutenoate, 4-diethylphosphono-3-methyl-2-butenoic acid esters, methyl 2-diethylphosphonoacetate, ethyl 2-diethylphosphonoacetate, 4-diethylphosphono-2- or 4-diethylphosphono-3-methyl-2-butenal acetals.

To prepare polyenecarbonyl compounds of the formula III mainly having the all-E configuration, the higher carbonyl compounds of the formula IV or V must also mainly have the all-E configuration. When using compounds having only one double bond, isomerizations in favor of an all-E configuration additionally occur in alkaline medium during the reaction according to the invention, such that, for example, in the Horner-Emmons reaction of $C_{25}$-aldehyde or $C_{30}$-aldehyde with alkyl 4-dialkylphosphono-2-methyl-2-butenoates the $C_5$- building block can be employed in an E/Z ratio from 2:1 to 100:1 and in spite of this all-E selectivities from 85 to 95% are obtained.

For safety reasons, the oxygen is in general not used in pure form, but preferably as an oxygen-inert gas mixture. Nitrogen is suggested as an inert gas. Preferably, oxygen is used in a mixture with nitrogen in the ratio of $N_2$ to $O_2$ of from 1 to 1–100:1, preferably approximately 95 to 5% by volume (lean air). The oxygen or the oxygen-containing gas mixture can be passed over the stirred reaction mixture or else passed into the reaction mixture. The action of the oxygen is dependent on its solubility, or on its partial pressure in the reaction mixture. For these reasons, it is also more advantageous to pass the oxygen into the reaction mixture instead of only over it.

It was very surprising that the oxygen in the process according to the invention exerts such an advantageous effect. In general, it is advisable when handling polyenes to work with exclusion of oxygen (cf. Houben-Weyl 5/ld page 13), as the polyenes frequently contain oxidation-sensitive double bonds.

Surprisingly, nitric oxide or a nitric oxide-inert gas mixture also exerts a catalytic effect favoring the formation of a double bond of E configuration in aldol or Horner-Emmons reactions. The nitric oxide, preferably in a mixture with an inert gas such as $N_2$, can be passed into the reaction mixture continuously. In the batchwise procedure it is sufficient if the nitric oxide needed is passed into the reaction vessel before the reaction and ensures that it cannot escape during the reaction.

The mechanism of action of the process according to the invention is still not known. Besides oxygen and NO, catalysts which can be employed are stable radicals in which a nitrogen radical or an N-oxyl are present in the molecule. When using stable radicals, the reaction can be carried out under inert gas protection. Preferably, stable radicals of the general formula I used are di-tert-butylamine-N-oxyl of the formula Ia; 2,2,6,6-tetramethyl-piperidine-N-oxyls of the formula Ib

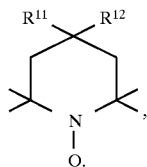

(Ib)

where $R^{11}$ is hydrogen
and $R^{12}$ is hydrogen, or a hydroxyl, alkoxy, acetoxy, amino, cyano or carboxyl group, oder else $R^{11}$ and $R^{12}$ together are an oxo group;

2,2,5,5-tetramethylpyrrolidine-N-oxyls of the formula Ic

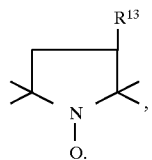

(Ic)

where $R^{13}$ is hydrogen or one of the groups indicated above for $R^{12}$ or
2,5-dihydro-2,2,5,5-tetramethyl-1H-pyrrole-N-oxyls of the formula Id

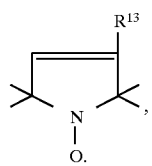

(Id)

where $R^{13}$ is hydrogen or one of the groups indicated above for $R^{12}$.

Particularly suitable stable radicals which may be mentioned, for example, are:

2,2,6,6-tetramethylpiperidine-N-oxyl (TEMPO), 4-hydroxy-2,2,6,6-tetramethylpiperidine-N-oxyl (4—OH—TEMPO), or esters with mono- or dibasic carboxylic acids thereof, such as the commercially available bis(1-oxyl-2,2,6,6-tetramethyl-piperidin-4-yl) sebacate, 4-oxo-2,2,6,6-tetramethylpiperidine-N-oxyl, 3-carboxy-2,2,5,5-tetramethylpyrroline-N-oxyl, 3-aminocarbonyl-2,5-dihydro-2,2,5,5-tetramethyl-1H-pyrrole-N-oxyl, di-tert-butylamine-N-oxyl or 2,2-diphenyl-1-picrylhydrazyl.

In general, the stable radicals are also used in amounts from 0.3 to 10 mol %, preferably 0.5 to 6 mol %, in particular 1 to 5 mol %, based on the polycarbonyl compound of the formula IV or V.

Depending on the nature of the reaction and of the reaction components, the reaction times are very different. For example, in the reaction of β-apo-12'-carotenal ($C_{25}$-aldehyde) or β-apo-8'-carotenal ($C_{30}$-aldehyde) with ethyl 4-diethylphosphono-2-meth-yl-2E-butenoate, ie. in a Horner-Emmons reaction with a $C_5$-phosphonate, they are in general from 1 to 20 hours, preferably 2 to 5 hours. When using the stable radicals in amount of less than 1 mol %, however, the reaction times are very much longer if it is wished to achieve optimum all-E selectivities.

Suitable catalysts for carrying out all-E selective Horner-Emmons reactions are very generally compounds which act themselves as oxidants and can easily be converted into the reduced form or into the hydro derivatives, but do not cause any oxidations or additions to the polyene building block. This also applies to quinones and quinone imines. Quinones and quinone imines are generally known, frequently physiologically active compounds. The biologically active quinones are derived essentially from 3 quinone nuclei, 1,4-naphthoquinone, methyl-substituted 1,4-benzoquinone and methyl- and methoxy-substituted 1,4-benzoquinone. They can contain a phytyl or derived phytyl group or a multiisoprenyl group. Mention may also be made of tocoquinones, such as vitamin $E_2$ (50), which is derived from 2,3,5-trimethyl-1,4-benzoquin-one; plastoquinones, which are derived from 2,3-dimethyl-1,4-benzoquinone; ubiquinones, such as coenzyme Q10, coenzyme Q6 or coenzyme Q0, which are derived from 2,3-dimethoxy-5-methyl- 1,4-benzoquinone, menaquinones, such as vitamin $K_2$ (50) and vitamin $K_2$ (30), which are derived from 2-methylnaphtho-1,4-quinone and phylloquinones, such as vitamin $K_1$, which are derived from a phytyl-substituted 2-methylnaphtho-1,4-quinone. With respect to more detailed information about the structure of biologically active quinones, refer to the "Handbuch zur Anwendung der Nomenklatur organisch-chemischer Verbindungen" [Handbook on the use of the nomenclature of organic chemical compounds] by W. Liebscher, Akademie-Verlag, Berlin 1979, pages 838 to 847.

Particularly suitable quinones or quinone imines are those of the general formula X or XI

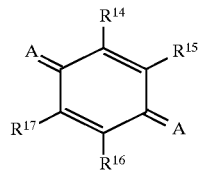
(X)

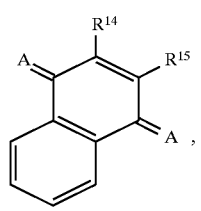
(XI)

where A is =O, =NH or =N—$R^5$, in which $R^5$ is an alkyl group or else $R^5$, together with one of the adjacent radicals $R^{14}$ to $R^{17}$, forms an alkylene radical or alkenylene radical having 2 or 3 C atoms, which can be substituted by halogen, $C_1$- to $C_4$-alkyl groups or $C_1$- to $C_4$-alkoxy groups; $R^{14}$ to $R^{17}$ are hydrogen, halogen or an alkyl, alkenyl, cycloalkyl, alkoxy, alkoxycarbonyl, cyano, acyloxy, aryl or heteroaryl group, it being possible for $R^2$ additionally to be a phytyl group, a group derived from the phytyl group, an isoprenyl group or a multiisoprenyl group.

Both electron-rich quinones or quinone derivatives of the formula I or II, such as coenzyme Q0, coenzyme Q10 or tocoquinones, and also electron-deficient quinones or quinone derivatives, such as tetrachloro-1,4-benzoquinone or dichlorodicyano-1,4-benzoquinones are suitable for the process according to the invention.

It was particularly surprising to find that even strong oxidants, such as chloranil (tetrachloro-1,4-benzoquinone) or dichloro-dicyanobenzoquinones (DDQ) have a high activity and selectivity, ie. have an all-E selective action without causing side reactions.

Advantageously, quinolones of the general formula Xa according to the invention are used

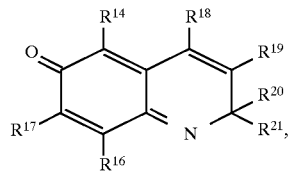
(Xa)

where $R^{14}$, $R^{16}$ and $R^{17}$ have the meanings indicated above and $R^{18}$ to $R^{21}$ are $C_1$- to $C_4$-alkyl or alkoxy groups or halogen, in particular the quinolone of the formula Xb

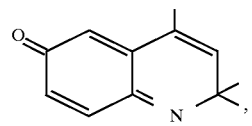
(Xb)

which can be derived from the known antioxidative stabilizer ethoxyquin and is known as a metabolite of ethoxyquin (cf. Xenobiotica 9 (1979), pages 649 to 57). Ethoxyquin itself only causes a moderate improvement in the all-E selectivity, while the quinolone Ib is to be included in the most active catalysts.

Further active derivatives of ethoxyquin are the dimers of the formulae XIIa and XIIb

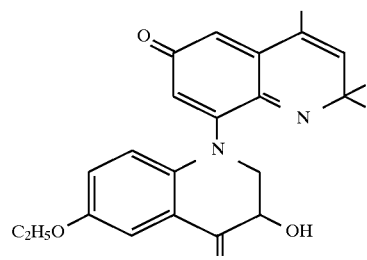
(XIIa)

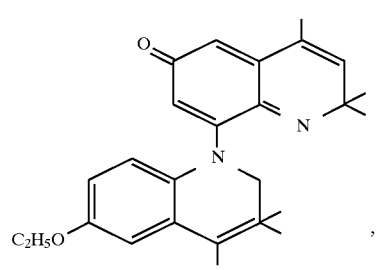
(XIIb)

and N-oxides of the general formula X

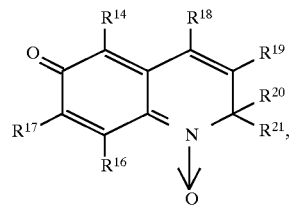
(XIII)

where $R^{14}$ and $R^{16}$ to $R^{21}$ have the meanings indicated above, but in particular are $C_1$- to $C_4$-alkyl or alkoxy groups or halogen.

Besides the para-quinones, however, ortho-quinones can also be employed according to the invention, as these too have very high redox potentials. With respect to further details about ortho-quinones refer to Houben-Weyl Vol. 7/3b, pages 3 to 6.

Surprisingly, individual hydroquinones, such as coenzyme Q10 hydroquinone, also have a higher activity. Possibly, these are those quinones which can be converted particularly easily to quinones.

Suitable quinoid compounds which may be mentioned in particular are: 1,4-benzoquinone, dimethyl-1,4-benzoquinone, trimethyl-1,4-benzoquinone, naphthoquinone, tetrachloro-1,4-benzo- quinone, tocoquinone acetate, phytyltrimethyl-1,4-benzoquinone, quinones of the vitamin K series and coenzyme Q10, coenzyme Q0 or 2,2,4-trimethyl-6(H)-quinolone.

The quinones and quinone imines are also in general employed in amounts from 0.3 to 10 mol %, preferably 0.5 to 6 mol %, in particular 1.0 to 5 mol %, based on the carbonyl compound employed.

Depending on the nature of the reaction and the reaction components, the reaction times are very different. For example, in the reaction of β-apo-12'-carotenal ($C_{25}$-aldehyde) or β-apo-8'carotenal ($C_{30}$-aldeyhde) with ethyl 4-diethylphosphono-2-methyl-2E-butenoate, ie. in a Horner-Emmons reaction with $C_5$-phosphonate, they are in general 1 to 20 hours, preferably 2 to 5 hours. When using the quinones or quinone derivatives in amounts of less than 0.5 mol %, however, the reaction times are longer if it is wished to achieve optimum all-E selectivities.

Both oxygen and NO, stable free radicals, quinones, quinone derivatives and coenzyme Q10 hydroquinone are suitable as catalysts for carrying out Horner-Emmons reactions. On the other hand, $O_2$ and NO are preferred for carrying out aldol condensations.

To carry out the reaction according to the invention, in general a procedure is used which is known and customary for the aldol condensation or the Horner-Emmons reaction, only during the reaction oxygen or an oxygen-inert gas mixture or nitric oxide or a nitric oxide-inert gas mixture is passed over the reaction mixture or into the reaction mixture and/or the reaction is carried out in the presence of the claimed stable radicals, quin-ones, quinone derivatives or coenzyme Q10 hydroquinone. When using stable radicals, quinones, quinone derivatives or coenzyme Q10 hydroquinone, the reaction is in general carried out with inert gas protection.

An aldol condensation is understood in the context of the present invention as meaning the coupling of the carbonyl compound of the formula IV with a compound of the general formula V, where Z is hydrogen, as a CH-active compound in the presence of a strong base. Strong bases which can be used are, in particular, alkali metal hydroxides, alkali metal alkoxides, alkali hydrides or alkali metal hexaalkylbissilazides. In isolated cases the use of a weak base, such as sodium carbonate, is also sufficient.

The reaction is in general carried out in a solvent, but also takes place in some cases without solvent. In many cases an excess of the more stable starting compound can also be used as a solvent. Suitable solvents are: acyclic, cyclic or aromatic hydrocarbons or halohydrocarbons, such as dichloroethylene, alkanols, such as methanol, ethanol or isopropanol, or mixtures of the solvents mentioned or else polar aprotic solvents, such as tetrahydrofuran, dimethylformamide or diethoxyethane.

To carry out the reaction, a procedure is in general used in which a solution of approximately equimolar amounts of the base is slowly added to the mixture of the starting compounds in a solvent in the presence of $O_2$, NO or one of the claimed catalysts and the reaction mixture is worked up in a manner known per se. However, in many cases it is also possible to initially introduce one reactant with the base and to slowly add the second reactant.

The reaction temperatures during the reaction should be from approximately −70 to 100° C., preferably −20° to 70° C.

Depending on the nature of the reactions, the reaction temperatures and the amount of catalyst, the reaction times are from 0.5 to 24 hours, preferably 1 to 10 hours. With respect to further details about aldol condensations, refer to Houben-Weyl, Vol. 5/1 (1972) page 142 to 144.

A Horner-Emmons reaction is understood in the context of the present invention as meaning the reaction of a carbonyl compound of the formula IV with a compound of the formula V, where Z is a dialkylphosphono group, in the presence of a base.

Suitable strong bases which may be mentioned in this case are also all alkali metal hydroxides, alkali metal alkoxides, alkali metal hydrides and alkali metal hexaalkylbissilazides and also $LiNH_2$ and $NaNH_2$, and in the isolated case also alkali metal carbonates. The reaction is in general carried out in a solvent, but also takes place in some cases without solvent. The solvent employed can in general be the solvent mentioned above for the aldol condensation. The reaction is particularly advantageously carried out in hydrocarbons or in mixtures of hydrocarbons and alkanols.

In this case, too, a procedure is in general used in which a solution of approximately equimolar amounts of the strong base is slowly added to the mixture of the starting compounds in a suitable solvent in the presence of $O_2$, NO and/or in the presence of one of the compounds claimed as a catalyst and, after complete reaction of the reaction mixture, worked up in a manner known per se for Horner-Emmons reactions. In this case, too, it is, however, possible in many cases for the more alkali-stable reactants to be initially introduced with the base and the other reactants to be slowly added to the mixture.

The process according to the invention is of particular importance for the preparation of a β-apo-8'carotenic acid ester of the formula VI

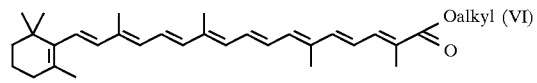

having an all-E content of greater than 85% by reaction of β-apo-12'-carotenal ($C_{25}$-aldehyde) having an all-E content of greater than 85% with an alkyl 4-dialkylphosphono-2-methyl-2-butenoate in a Horner-Emmons reaction, for the preparation of neurosporaxanthic acid esters of the formula VII ($C_{35}$-esters)

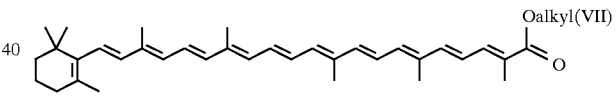

having an all-E content of greater than 85% by reaction of β-apo-8'-carotenal ($C_{30}$-aldehyde) having an all-E content of greater than 85% with an alkyl 4-dialkylphosphono-2-methyl-2-butenoate in a Horner-Emmons reaction and the preparation of citranaxanthin having an all-E content of greater than 85% by reaction of β-apo-8'-carotenal having an all-E content of greater than 85% with acetone in an aldol condensation.

As the all-E isomers crystallize significantly better and more easily in suitable solvents in the case of said long-chain polyenecarbonyl compounds of the general formula III, higher yields of the desired polyenecarbonyl compound in crystalline form are in general also obtained. When using stable radicals, quin-ones, quinone derivatives or coenzyme Q10 hydroquinone as a catalyst, during working up these in general remain virtually quantitatively in the wash liquor or in the mother liquor.

Using the process according to the invention, polyenecarbonyl compounds of the general formula III can be obtained, such as the β-apo-8'-carotenic acid esters, neurosporaxanthin acid esters and citranaxanthin having an all-E content of up to 95% which are all very much desired as foodstuff colorants, if the longer-chain starting products are mainly present in the all-E configuration.

EXAMPLE 1

Preparation of ethyl β-apo-8'-carotinate ($C_{30}$-ethyl ester) by Horner-Emmons reaction

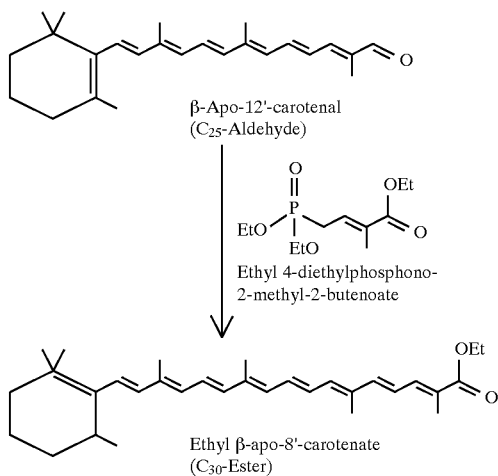

β-Apo-12'-carotenal ($C_{25}$-Aldehyde)

Ethyl 4-diethylphosphono-2-methyl-2-butenoate

Ethyl β-apo-8'-carotenate ($C_{30}$-Ester)

Variant A (use of 1 mol % 4—OH—TEMPO (reaction time: 5 hours)

1.72 g (10 mmol) of 4-hydroxy-2,2,6,6-tetramethyl-piperidine-N-oxyl (4-OH-TEMPO) in 5 ml of ethanol were added at 25° C. under a nitrogen atmosphere to a mash of 350.5 g (1 mol) of crystalline β-apo-12'carotenal ($C_{25}$-aldehyde) in 1200 ml of technical heptane. 289 g (1.05 mol of a 96% ethyl 4-diethylphosphono-2-methyl-2E-butenoate ($C_5$-ester phosphonate) were then added. 500 ml of a 20% strength sodium ethoxide solution (1.28 mol; density 0.873 kg/l) were then metered in at 25°–30° C. in the course of 4 hours (h) with good $N_2$ gassing (about 8 l/h). The mixture was then stirred at 25° C. for 1 h. The all-E content in the $C_{30}$-ester was 92.2% according to HPLC.

The organic phase was then washed with dilute aqueous sulfuric acid and 60% strength aqueous methanol.

After addition of methanol, the ethyl β-apo-8'-carotenate obtained was filtered off and washed twice with methanol. Drying to constant weight was carried out under $N_2$ at 50° C.

Yield: 390.2 g (84.7%); all-E content: 99.7%.

Variant B (use of 0.5 mol % TEMPO; reaction time 76 h)

0.79 g (5 mmol) of 2,2,6,6-tetramethylpiperidine-N-oxyl (TEMPO) in 5 ml of ethanol was added at 25° C. under a nitrogen atmosphere to a mash of 350.5 g (1 mol) of crystalline $C_{25}$-aldehyde in 1200 ml of technical heptane. 289 g (1.05 mol) of a 96% $C_5$-ester phosphonate were then added.

500 ml of a 20% strength NaOEt solution (1.28 mol; density 0.873 kg/l) were metered in at 25° C. in the course of 76 h with good $N_2$ gassing. The all-E content in the $C_{30}$-ester was 92.3% according to HPLC. Working up was carried out in a similar manner to variant A.

Yield: 380.4 g (82.6%); all-E content: 99.3%.

To determine the effect of the amount of TEMPO or 4-hydroxy-TEMPO (4—OH—TEMPO) employed, the $C_{25}$-aldehyde β-apo-12'-carotenal was reacted with the $C_5$-ester phosphonate in a similar manner to Example 1, variants A and B in the presence of the amounts of TEMPO or 4-hydroxy-TEMPO evident from Table 1 or Table 2 and the all-E content in the $C_{30}$-ester was determined by means of HPLC in the reaction mixture obtained. The results are compiled in Tables 1 and 2.

TABLE 1

As the all-E isomers crystallize significantly better and more easily in suitable solvents in the case of said long-chain polyenecarbonyl compounds of the general formula III, high yields of the desired polyenecarbonyl compound in crystalline form are in general also obtained. When using stable free radicals, quin-ones, quinone derivatives or coenzyme Q10 hydroquinone as a catalyst, during working up these in general remain virtually quantitatively in the wash liquor or in the mother liquor.
Effects of the amount of TEMPO on the E/Z ratio in the Horner-Emmons reaction described

| Example 1 | Variant (reaction time) | Procedure | $C_5$-Ester phosphonate: purity (E/Z ratio) | TEMPO [mol % based on $C_{25}$ aldehyde] | all-E content of $C_{25}$ aldehyde | all-E-content of the $C_{30}$ ester |
|---|---|---|---|---|---|---|
| a | A (5 h) | under $N_2$ | 96% (18/1) | 5 mol % | 99.0% | 94.6% |
| b | A (5 h) | under $N_2$ | 96% (18/1) | 5 mol % | 99.0% | 94.3% |
| c | A (5 h) | under $N_2$ | 97% (7/1) | 5 mol % | 99.0% | 94.9% |
| d | A (5 h) | under $N_2$ | 96% (18/1) | 3 mol % | 99.0% | 93.5% |
| e | A (5 h) | under $N_2$ | 96% (18/1) | 1 mol % | 99.0% | 88.5% |
| f | A (5 h) | under $N_2$ | 96% (18/1) | 0.5 mol % | 99.0% | 77.5% |
| g | B (76 h) | under $N_2$ | 96% (18/1) | 0.5 mol % | 98.6% | 92.3% |

TABLE 2

Effect of the amount of 4-OH-TEMPO on the E/Z ratio in the Horner-Emmons reaction described

| Example 1 | Variant (reaction time) | Procedure | $C_5$-Ester phosphonate: purity (E/Z ratio) | 4-OH-TEMPO [mol % based on $C_{25}$ aldehyde] | all-E content of $C_{25}$ aldehyde | all-E content of $C_{30}$ ester |
|---|---|---|---|---|---|---|
| h | A (5 h) | under $N_2$ | 96% (18/1) | 5 mol % | 99.0% | 95.0% |
| i | A (5 h) | under $N_2$ | 96% (18/1) | 3 mol % | 99.0% | 94.7% |
| j | A (5 h) | under $N_2$ | 96% (18/1) | 1 mol % | 99.0% | 92.2% |
| k | A (5 h) | under $N_2$ | 96% (18/1) | 0.5 mol % | 99.0% | 77.4% |

In a similar manner to Example 1, variant A, the $C_{25}$-aldehyde was reacted with the $C_5$-ester phosphonate without addition of oxygen or stable radicals (comparison experiments) or in the presence of various stable radicals or radical scavengers and the all-E content in the $C_{30}$-ester was determined by means of HPLC in the reaction mixture obtained. The results are compiled in Table 3. Experiments with inactive stable radicals or radical scavengers or antioxidants are comparison experiments and are given an asterisk *. The oxygen was used in all experiments in the form of lean air (95% $N_2$+5% $O_2$). In the case of the use of NO gas, 120 ml of NO were passed in in 5 to 10 min, care being taken that the NO can leave the reaction space during the addition of base.

The name 3-carboxyproxyl or 3-carbamoylproxyl in this case stands for 3-carboxy- or 3-carbamoyloxy-2,2,5,5-tetramethylpyrrolidine-N-oxyl and the name 3-carbamoyldoxyl for 3-carbamoyl-2,5-dihydro-2,2,5,5-tetramethyl-pyrrole-N-oxyl.

TABLE 3

Effect of free radicals or of radical scavengers on the E/Z ratio in the Horner-Emmons reaction described

| Example 1 | Variant (reaction time) | Procedure | $C_5$-ester phosphonate: purity (E/Z ratio) | Additive [mol % based on $C_{25}$-ald.] | $C_{25}$-aldehyde [all-E content] | $C_{30}$-ester [all-E content] |
|---|---|---|---|---|---|---|
| l | A (5 h) | under $N_2$ | 96% (18/1) | —* (comparison experiment) | 99.0% | 72.4% |
| m | A (5 h) | under $N_2$ | 96% (18/1) | 2 mol %* tocopherol | 99.0% | 72.4% |
| n | A (5 h) | under $N_2$ | 96% (18/1) | 5 mol %* N-methylmorpholine-N-oxide | 99.0% | 76.5% |
| o | A (5 h) | under $N_2$ | 96% (18/1) | 5 mol %* dipotassium nitroso-disulfonate (Fremy's salt) | 99.0% | 76.7% |
| p | A (5 h) | under $N_2$ | 96% (18/1) | 5 mol %* triacetoneaminoalcohol | 99.0% | 76.8% |
| q | A (5 h) | under $N_2$ | 96% (18/1) | 5 mol %* galvinoxyl | 99.0% | 78.5% |
| r | A (5 h) | under $N_2$ | 96% (18/1) | 5 mol %* nitrosobenzene | 99.0% | 79.6% |
| s | A (5 h) | under $N_2$ | 96% (18/1) | 1.8 mol % $O_2$ | 99.0% | 86.6% |
| t | A (5 h) | under $N_2$ | 96% (18/1) | 5 mol % 3-carboxyproxyl | 99.0% | 90.5% |
| u | A (5 h) | under $N_2$ | 96% (18/1) | 5 mol % 2,2-diphenyl-1-picrylhydrazyl | 99.0% | 92.9% |
| v | A (5 h) | under $N_2$ | 96% (18/1) | 7.2 mol % $O_2$ | 99.0% | 93.8% |
| w | A (5 h) | under $N_2$ | 96% (18/1) | 5 mol % TEMPO | 99.0% | 94.6% |
| x | A (5 h) | under $N_2$ | 97% (7/1) | 5 mol % TEMPO | 99.0% | 94.9% |
| y | A (5 h) | under $N_2$ | 96% (18/1) | 5 mol % 4-OH-TEMPO | 99.0% | 95.0% |
| z | A (5 h) | under $N_2$ | 96% (18/1) | 5 mol % $H_2O_2$-urea adducts | 99.0% | 84.1% |
| aa | A (5 h) | under $N_2$ | 96% (18/1) | 5 mol % NO | 99.0% | 89.6% |
| ab | A (5 h) | under $N_2$ | 96% (18/1) | 5 mol % di-tert-butylnitroxyl | 99.0% | 93.9% |
| ac | A (5 h) | under $N_2$ | 96% (18/1) | 5 mol % 3-carbamoylproxyl | 99.0% | 92.2% |
| ad | A (5 h) | under $N_2$ | 96% (18/1) | 5 mol % 3-carbamoyldoxyl | 99.0% | 92.8% |

* = comparison experiments

EXAMPLE 2

Preparation of ethyl β-apo-8'-carotenate a) in the presence of $O_2$ 70 g of β-apo-12'-carotenal (E content 98%) were suspended in 300 ml of heptane and treated with 60 g of a 96% ethyl 4-diethylphosphono-2-methyl-2E-butenoate. 110 ml of a 20% strength sodium ethoxide solution were added dropwise at 20°–25° C. in the course of 4 h while stirring and passing in 10 l/h of lean air (mixture of $N_2$ and air in the ratio 3:1). The organic phase was then washed with dilute sulfuric acid and with 60% strength aqueous methanol. The all-E content in the ethyl β-apo-8'-carotenate obtained was 94.7% and the Z content 5.3% according to HPLC.

After cooling to 0° C., filtering off with suction and drying the crystals in a stream of $N_2$, 79.7 g of pure crystalline ethyl all-E-β-apo-8'-carotenate were obtained (all-E content: >98%). This corresponds to a yield of 86.6% of theory, based on β-apo-12'-carotenal.

b) Comparison example (under an $N_2$ atmosphere)

The procedure was carried out as described above under a), only instead of lean air 10 l/h of nitrogen were passed into the reaction mixture. The all-E content in the ethyl β-apo-8'-carotenate obtained was 77.4% and the content of ethyl Z-β-apo-8'-carotenate isomers was 22.6% according to HPLC.

Under identical crystallization conditions, it was possible to obtain only 63 g of a pure crystalline ethyl all-E-β-apo-8'-carotenate. This corresponds to a yield of only 68.5%, based on β-apo-12'-carotenal employed.

EXAMPLE 3

Preparation of ethyl β-apo-4'-carotenate ($C_{35}$-ester) by Horner-Emmons reaction

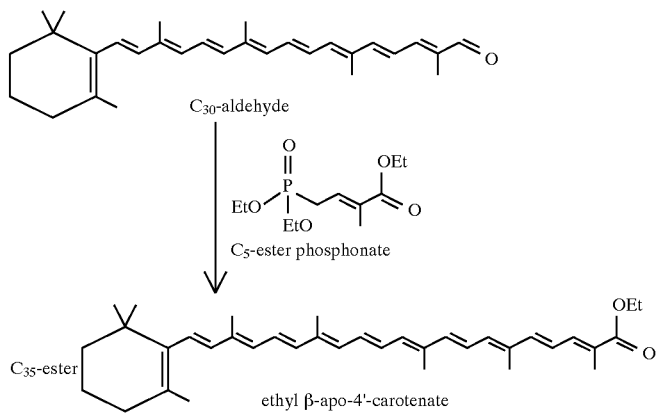

7.8 g (50 mmol) of TEMPO were added at 25° C. under a nitrogen atmosphere to a mash of 419.6 g (1 mol) of a 99.3% pure crystalline $C_{30}$-aldehyde in 1200 ml of technical heptane. 289 g (1.05 mol) of a 96% $C_5$-ester phosphonate were then added. 500 ml of a 20% strength NaOEt solution (1.28 mol; density 0.873 kg/l) were then metered in at 25°–30° C. in the course of 4 h with good $N_2$ gassing (about 8 l/h). A very substantial crystal mash formed during the reaction. The all-E content in the $C_{35}$-ester after the end of the addition of base was 94.0% according to HPLC.

The separated organic phase was then washed with dilute aqueous sulfuric acid and with a mixture of methanol and dilute aqueous sulfuric acid.

After addition of heptane and methanol, the product was filtered off and washed with water. Drying: under $N_2$ at 50° C./1 mbar to constant weight.

Yield: 495.2 g (94.0%) of crystallizate; all-E content: 97.5%; m.p. 140°–141° C.

$E^1$ (1%, 1 cm): 2656 (cyclohexane; 479 nm); content 98.4% calc. with $E^1$=2700

An approximately identical result was obtained when using 5 liters (l) of lean air per hour and mol instead of TEMPO.

EXAMPLE 4

Preparation of citranaxanthin by aldol condensation

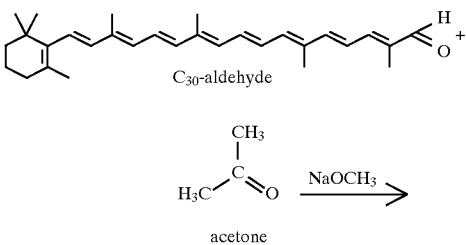

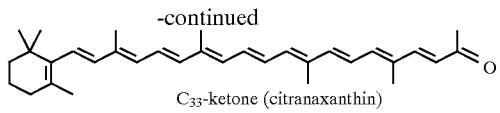

41.67 g (0.1 mol) of $C_{30}$-aldehyde in each case were suspended in a mixture of 417 ml of acetone and 208 ml of heptane at room temperature (RT) under lean air or nitrogen gassing (10 liters/h) according to the data in the following table. The suspension was warmed to 40° C. and 63 ml of a 1% strength solution of the base in methanol which is apparent from the table were added dropwise in the course of 6 h under lean air or $N_2$ gassing. Samples were taken hourly to determine the course of the reaction by means of HPLC.

The crystallized citranaxanthin was filtered off with suction and washed with methanol. Drying was carried out in an $N_2$ stream at 50° C./1 mbar. The yields were only determined in the reaction mixtures which proceeded without appreciable isomerization.

TABLE 4

| Example 4 | $C_{30}$-aldehyde [% all-E-] | Gassing | Base [mol % based on $C_{30}$ aldehyde] | Reaction time [h] | all-E isomers [%] | Z isomers [%] | Yield [%] |
|---|---|---|---|---|---|---|---|
| a | 99% | lean air (10 l/h) | 1% strength NaOCH$_3$; 9.2 mol % | 6 | 97 | 2.5 | 90% |

TABLE 4-continued

| Example 4 | $C_{30}$-aldehyde [% all-E-] | Gassing | Base [mol % based on $C_{30}$ aldehyde] | Reaction time [h] | all-E isomers [%] | Z isomers [%] | Yield [%] |
|---|---|---|---|---|---|---|---|
| b* | 99% | $N_2$ | 1% strength NaOCH$_3$; 9.2 mol % | 2 | 62.2 | 37.8 | 61% |
| c* | 93.2 (6.8% 9-Z) | $N_2$ | 1% strength NaOH; 12.3 mol % | 4 | 63.6 | 4.9% 9-Z-, 31.8% other isomers | 62% |
| d | 93.2 (6.8% 9-Z) | lean air (10 l/h) | 1% strength NaOH; 12.5 mol % | 6 | 92.2 | 6% 9-Z, 1.8% other Z isomers | 80–85% |
| e* | 93.2 (6.8% 9-Z) | $N_2$ | 1% strength KOH; 7.6 mol % | 6 | 61.9 | 5.9% 9-Z-, 32.2% other Z isomers | 60% |
| f | 93.2 (6.8% 9-Z) | lean air (10 l/h) | 1% strength KOH; 7.6 mol % | 15 | 92 | 6.4% 9-Z-, 1.6% other Z isomers | 75% |
| g | 93.2 (6.8% 9-Z) | lean air (10 l/h) | 1% strength NaOH; 12.5 mol % | 4 | 92 | 6.2% 9-Z-, 1.8% other Z isomers | 80–85% |

\* = comparison example

EXAMPLE 5
Preparation of Citranaxanthin 33 g (0.08 mol) of $C_{30}$-aldehyde (all-E content 98%) in each case were suspended in 575 ml of acetone, 2 g of BHT (butylated hydroxytoluene as an antioxidant) and the amount of TEMPO apparent from Table 5 which follows were added if desired and the reaction mixture obtained was warmed to 43° C. 5.2 g of a 50% strength by weight aqueous NaOH (0.07 mmol) were added dropwise at this temperature in the course of the reaction time indicated in Table 5 which follows.

The reaction mixture was then cooled to 20° C. in the course of 30 min and stirred at 20° C. for a further 30 min. The content of the reaction mixture of all-E-citranaxanthin and the content of other citranaxanthin isomers was determined by means of HPLC and is indicated in Table 5 which follows.

The mixture was then filtered through a suction filter. The filter cake was washed with methanol and dried at about 50° C. in a drying oven.

EXAMPLE 6
Preparation of ethyl β-apo-8'-carotenate by Horner-Emmons reaction in the presence of bis(1-oxyl-2,2,6,6-tetramethylpiperidin-4-yl) sebacate 1.28 g (2.5 mmol) of bis(1-oxyl-2,2,6,6-tetramethylpiperidin-4-yl) in 5 ml of ethanol were added at 25° C. under a nitrogen atmosphere to a mash of 25.05 g (100 mmol) of crystalline β-apo-12'-carotenal in 120 ml of technical heptane. 30.3 g (110 mmol) of a 96% strength $C_5$-ester phosphonate were then added. 50 ml of 20% strength sodium ethoxide solution (128 mmol) were metered in at 25°–30° C. in the course of 4 h with $N_2$ gassing. The mixture was then stirred at 25° C. for 1 h. The all-E content in the $C_{30}$-ester was 94.9% according to HPLC.

The organic phase was then washed with dilute aqueous sulfuric acid and 60% strength methanol.

After addition of methanol, the ethyl β-apo-8'-carotenate obtained was filtered off and washed twice with methanol. Drying was carried out to constant weight.

Yield: 39.5 g (85.8%); all-E content: 99.8%.

EXAMPLE 7
Preparation of ethyl β-apo-8'-carotenate ($C_{30}$-ethyl ester) by Horner-Emmons reaction in the presence of 2,2,4-trimethyl-6(H)-quinolone 1.96 g (10 mmol) of 2,2,4-trimethyl-6(H)-quinolone in 5 ml of ethanol were added at 25° C. under an argon atmosphere to a mash of 350.5 g (1 mol) of crystalline β-apo-12'-carotenal ($C_{25}$-aldehyde) in 1200 ml of technical heptane. 320.8 g (1.1 mol) of a 96% ethyl 4-diethylphosphono-2-methyl-2E-butenate ($C_5$-ester phosphonate) were then added. 500 ml of a 20% strength sodium ethoxide solution (1.28 mol) were then metered in at 25°–30° C. in the course of 4 hours (h) with argon gassing. The mixture was then heated to 55° C. The all-E content in the $C_{30}$-ester was 94.8% according to HPLC.

The organic phase was then washed at 55° C. with dilute aqueous sulfuric acid and 60% strength aqueous methanol.

After addition of 1 l of methanol, the mixture was cooled to −5° C. and the ethyl β-apo-8'-carotenal was filtered off

TABLE 5

| Example 4 | "TEMPO" [mol %] | Gassing | Base | Reaction time [h (°C.)] | all-E isomer [%] | Other isomers [%] |
|---|---|---|---|---|---|---|
| a* | — (+2 g BHT) | $N_2$ | NaOH | 3 (43° C.) | 51.4 | 47.9 |
| b | 5 (+2 g BHT) | $N_2$ | NaOH | 3 (43° C.) | 71.7 | 26.9 |
| c* | — | $N_2$ | NaOH | 1 (43° C.) | 50.7 | 48.5 |
| d | 5 | $N_2$ | NaOH | 3 | 62.9 | 35.5 |
| e | 30 | $N_2$ | NaOH | 3 | 67.0 | 31.3 |
| f | 100 | $N_2$ | NaOH | 3 | 73.5 | 24.7 |

\* = Comparison example and washed with ethanol. Drying was carried out under N₂ at 50° C. to constant eight.

Yield: 401.3 g (87.1%); all-E content: 98.9%.

EXAMPLE 8
Preparation of ethyl β-apo-8'-carotenate ($C_{30}$-ethyl ester) by Horner-Emmons reaction in the presence of quinones, quinone derivatives and coenzyme Q10 hydroquinone The amounts apparent from Table 1 of the additive apparent from the table in 2 ml of ethanol were added at 25° C. under an argon atmosphere to a mash of 35.05 g (0.1 mol) of $C_{25}$-aldehyde in 120 ml of technical heptane. 30.3 g (110 mol) of a 96% $C_5$-ester phosphonate having the E/Z isomer ratio apparent from Table 6 were then added. 50 ml of a 20% strength sodium ethoxide solution (128 mmol) were metered in at 25°–30° C. in the course of 4 h under argon gassing. The mixture was then stirred at 25° C. for 1 h. The all-E content in the $C_{30}$-ester was determined in each case by means of HPLC. The results are shown in Table 6.

TABLE 6

Effect of quinones, quinone imines and coenzyme Q10 hydroquinone on the E/Z ratio in the Horner-Emmons-reaction described

| Example | Procedure | $C_5$-ester phosphonate: purity (E/Z ratio) | Additive [mol % based on $C_{25}$-aldehyde] | $C_{25}$-aldehyde [all-E content] | $C_{30}$-ester [all-E content] |
|---|---|---|---|---|---|
| 2a | under argon | 96% (25/1) | —* (comparison experiment) | 99.0% | 76% |
| 2b | under argon | 96% (25/1) | 5 mol % trimethyl-1,4-benzoquinone (TMC) | 99.0% | 90.2% |
| 2c | under argon | 96% (25/1) | 5 mol % coenzyme Q10 | 99.0% | 91.7% |
| 2d | under argon | 96% (25/1) | 5 mol % tetrachloro-1,4-benzoquinone | 99.0% | 91.6% |
| 2e | under argon | 96% (25/1) | 5 mol % tocoquinone acetate | 99.0% | 90.3% |
| 2f | under argon | 96% (25/1) | 5 mol % coenzyme Q0 | 99.0% | 88% |
| 2g | under argon | 96% (25/1) | 5 mol % 2-methyl-1,4-naphthoquinone | 99.0% | 88% |
| 2h | under argon | 96% (25/1) | 1 mol % 2,2,4-trimethyl-6(H)-quinolone | 99.0% | 94.8% |
| 2i | under argon | 96% (18/1) | 6 mol % 2,2,4-trimethyl-6(H)-quinolone | 98.7% | 93.7% |
| 2k | under argon | 96% (25/1) | 5 mol % coenzyme Q10 hydroquinone | 99.0% | 88.4% |

EXAMPLE 9
Preparation of ethyl β-apo-4'-carotenate (C35-ester) by Horner-Emmons reaction in the presence of quinones, quinone derivatives and coenzyme Q10 hydroquinone 41.67 g (100 mmol) of $C_{30}$-aldehyde were suspended in 400 ml of technical heptane and treated at room temperature (RT) under an argon atmosphere with 30.3 g (110 mmol) of 96% $C_5$-ester phosphonate and 5 mmol of the additives indicated in Table 7. 50 ml of a 20% strength sodiumethoxide solution were metered in in the course of 4 h. The mixture was stirred at RT for 16 h. The all-E contents in the product were determined by HPLC and compiled in Table 7.

TABLE 7

Effect of quinones, hydroquinones and quinone imines on the E/Z ratio in the Horner-Emmons reaction described

| Example | Procedure | $C_5$-ester phosphonate: purity (E/Z ratio) | Additive [mol % based on $C_{30}$-aldehyde] | $C_{30}$-aldehyde [all-E content] | $C_{35}$-ester [all-E content] | E/Z selectivity of the reaction based on $C_{30}$-aldehyde |
|---|---|---|---|---|---|---|
| 3a | under argon | 96% (25/1) | —* (comparison experiment) | 95.8% | 70% | 73% |
| 3b | under argon | 96% (25/1) | 5 mol % coenzyme Q10 | 95.8% | 83.5% | 87% |
| 3c | under argon | 96% (25/1) | 5 mol % 2,2,4-trimethyl-6(H)-quinolone | 95.8% | 88.6% | 92.5% |
| 3d | under argon | 96% (25/1) | 5 mol % coenzyme Q10 hydroquinone | 95.8% | 82.6% | 86% |

We claim:

1. A process for preparing polyenecarbonyl compounds of the formula III or the formula IX,

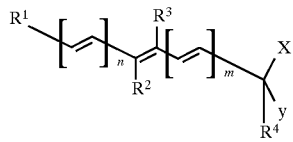

or

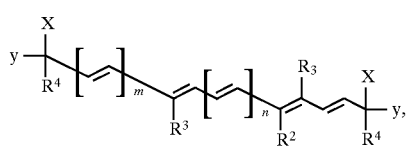

where $R^1$, $R^2$, $R^3$ and $R^4$ are hydrogen or an organic radial, n is an integer of from 3–10, m is an integer of from 0 to 10, n+m being at least 2, x and y are $C_1$–$C_4$-alkoxy or x and y together are oxygen or a radical —O—$CH_2$—$CH_2$—O—, —O—$CH_2$—$C(CH_3)_2$—$CH_2$—O—, —O—CH=CH—O— or —O—$CH_2$—$CH_2$—$CH_2$—O— which may be substituted by one or more methyl groups, and the hydrogen atoms in the brackets can be partly substituted by a methyl group, said compounds having a high all-E content and their acetals or ketals by a Horner-Emmons reaction or an aldol condensation of a suitable carbonyl compound with a suitable dialkyl phosphonate or of a suitable CH-acidic compound, which comprises carrying out the reaction, for the purposes of the preferred formation of a double bond having E configuration and in order to maintain the E configuration of the double bonds in the starting compounds as completely as possible, in the presence of one or more agents selected from the group consisting of oxygen, an oxygen-inert gas mixture, nitric oxide, a nitric oxide-inert gas mixture, a stable radical of the formula I

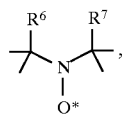

where $R^6$ and $R^7$ are a $C_1$-to $C_4$-alkyl group or else $R^6$ and $R^7$ are an ethylene group, propylene group, vinylene group or propenylene group, which can be substituted by alkyl, aryl, hydroxyl, alkoxy, silyloxy, oxo, amino, mercapto, alkylmercapto, cyano, carboxyl, aminocarbonyl (carbamoyl), heteroaryl or alkylcarbonyloxy groups; a stable radical of the formula II

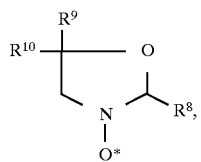

where $R^8$, $R^9$ and $R^{10}$ can have the meanings indicated above for $R^6$ and $R^7$; the stable radical 2,2-diphenyl-1-picrylhydrazyl, a hydrogen peroxide-urea adduct quinone, quinone derivatives and a coenzyme Q10 hydroquinone, the oxygen, the nitric oxide, the stable radicals or the hydrogen peroxide-urea adduct and the quinones, quinone derivatives or coenzyme Q10 hydroquinone being used in amounts from 0.3 to 10 mol %, based on the carbonyl compound employed.

2. A process as defined in claim 1, wherein the stable radical of the general formula I is di-tert-butylamine-N-oxyl of the formula Ia

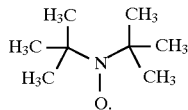

3. A process as defined in claim 1, wherein the stable radical of the formula I is a 2,2,6,6-tetramethylpiperidine-N-oxyl of the formula Ib

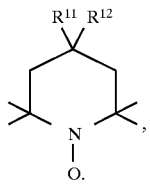

where $R^{11}$ is hydrogen
and $R^{12}$ is hydrogen, or a hydroxyl, alkoxy, acetoxy, amino, cyano or carboxyl group, or else $R^{11}$ and $R^{12}$ together are an oxo group.

4. A process as defined in claim 1, wherein the stable radical of the formula I is a 2,2,5,5-tetramethylpyrrolidine-N-oxyl of the formula Ic

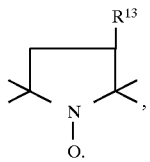

where $R^{13}$ is hydrogen or one of the groups indicated for $R^{12}$ in claim 3.

5. A process as defined in claim 1, wherein the stable radical of the formula I is a 2,5-dihydro-2,2,5,5-tetramethyl-1H-pyrrole-N-oxyl of the formula Id

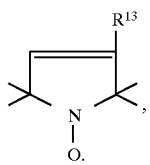

where $R^{13}$ has the meaning indicated in claim 4.

6. A process as defined in claim 1, wherein the reaction is carried out in the presence of quinones or quinone derivatives of the formula X or XI

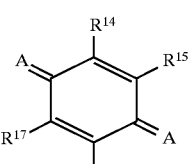

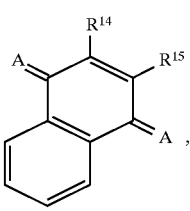

where A is =O, =NH or =N—$R^5$, in which $R^5$ is an alkyl group or else $R^5$ with one of the adjacent radicals $R^{14}$ to $R^{17}$ together form an alkylene radical having 2 or 3 C atoms, which can be substituted by halogen, $C_1$- to $C_4$-alkyl groups or $C_1$- to $C_4$-alkoxy groups, and R14 to $R^{17}$ are hydrogen, halogen or an alkyl, alkenyl, cycloalkyl, alkoxy, alkoxycarbonyl, cyano, acyloxy, aryl or heteroaryl group.

7. A process as defined in claim 1, wherein the reaction is carried out in an acyclic, a cyclic or an aromatic hydrocarbon or halohydrocarbon, or in alcohol or a polar aprotic solvent or a mixture of 2 or more of these solvents.

8. A process as defined in claim 1, wherein to prepare citranaxanthin of the formula VIII

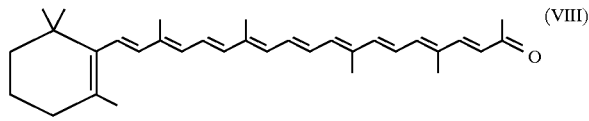
(VIII)

having an all-E content of greater than 85%, β-apo-8'-carotenal having an all-E content of greater than 85% is reacted with acetone in an aldol condensation in the presence of oxygen or an oxygen-inert gas mixture or nitric oxide or a nitric oxide-inert gas mixture.

9. A process as defined in claim 1, wherein $R^3$ is hydrogen, $C_1$–$C_4$-alkyl or $C_1$–$C_4$-alkoxy and wherein $R^4$ is hydrogen, $C_1$–$C_4$-alkyl or $C_1$–$C_4$-alkoxy.

10. A process as defined in claim 1, wherein $R^3$ is hydrogen, $C_1$–$C_4$-alkyl or $C_1$–$C_4$-alkoxy, $R^4$ is hydrogen, $C_1$-$C_4$-alkyl or $C_1$–C4-alkoxy, $R^1$ is

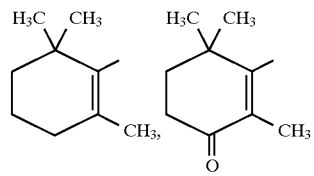

or

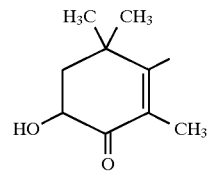

or is a formyl group, and $R^2$ is hydrogen or alkyl.

11. A process for preparing a β-apo-8'-carotenic acid ester of the formula VI

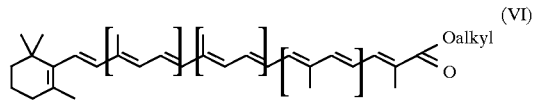
(VI)

having an all-E content of greater than 85%, which comprises reacting β-apo-12'-carotenal ($C_{25}$ aldehyde) having an all-E content of greater than 85% with an alkyl 4-dialkylphosphono-2-methyl-2-butenoate in a Horner-Emmons reaction in the presence of one or more agents selected from the group consisting of oxygen, an oxygen-inert gas mixtures nitric oxides a nitric oxide-inert gas mixture, 2,2,6,6-tetramethylpiperidine-N-oxyl (TEMPO), 4-hydroxy-2,2,6,6-tetra-methylpiperidine-N-oxyl (4-OH-TEMPO), 4-oxo-2,2,6,6-tetramethyl-piperidine-N-oxyl, 3-carboxy-2,2,5,5-tetramethylpyrrolidine-N-oxyl, 3-aminocarbonyl-2,2,5,5-tetramethylpyrrolidine-N-oxyl, 3-aminocarbonyl-2,5-dihydro-2,2,5,5-tetramethyl-1H-pyrrole-N-oxyl, di-tertbutylamine-N-oxyl and 2,2-diphenyl-1-picrylhydrazyl as a stable radical or in the presence of trimethyl-1,4-benzoquinone, coenzyme Q10, tetrachloro-1,4-benzoquinone, tocoquinone acetate, coeenzyme Q0 or 2,2,4-trimethyl-6(H)-quinolone as a quinone or quinone derivative.

12. A process for preparing a neurosporaxanthinic acid ester of the formula VII

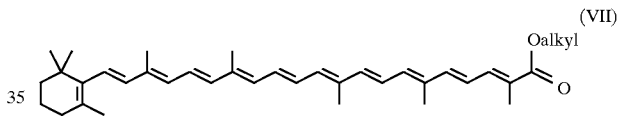
(VII)

having an all-E content of greater than 85% which process comprises reacting β-apo-8'-carotenal having an all-E content of greater than 85% with an alkyl 4-dialkylphosphono-2-methyl-2-butenoate in a Horner-Emmons reaction in the presence of oxygen or an oxygen-inert gas mixture or nitric oxide or a nitric oxide-inert gas mixture and/or in the presence of one of the stable radicals mentioned in claim 8 or else with one of the quinones or quinone derivatives mentioned in claim 8.

* * * * *